(12) United States Patent
Wong

(10) Patent No.: US 6,270,986 B1
(45) Date of Patent: Aug. 7, 2001

(54) METHOD OF PRESERVING BIOLOGICAL TISSUE SPECIMENS AND METHOD OF INFRARED SPECTROSCOPIC ANALYSIS WHICH AVOIDS THE EFFECTS OF POLYMORPHS

(76) Inventor: Patrick T. T. Wong, 35 MacNabb Place, Ottawa, Ontario (CA), K1L 8J5

( * ) Notice: Subject to any disclaimer, the term of this patent is extended or adjusted under 35 U.S.C. 154(b) by 0 days.

(21) Appl. No.: 09/250,253

(22) Filed: Feb. 16, 1999

(51) Int. Cl.[7] .................................................. G01N 1/30
(52) U.S. Cl. ................... 435/40.52; 435/40.5; 435/40.51
(58) Field of Search ......................... 435/34, 40.5, 40.51, 435/40.52; 250/338.1, 12, 339; 436/171; 600/473, 562

(56) References Cited

U.S. PATENT DOCUMENTS

| | | | |
|---|---|---|---|
| 5,030,560 | | 7/1991 | Sinor et al. .......................... 435/7.21 |
| 5,038,039 | * | 8/1991 | Wong et al. .......................... 250/339 |
| 5,168,162 | * | 12/1992 | Oong et al. .......................... 250/339 |
| 5,539,207 | * | 7/1996 | Wong ............................. 250/339.08 |
| 5,733,507 | * | 3/1998 | Zakim ................................. 422/101 |
| 5,733,739 | * | 3/1998 | Zakim et al. ........................... 435/29 |
| 5,976,885 | * | 11/1999 | Cohenford et al. .................... 436/63 |
| 6,031,232 | * | 2/2000 | Cohenford et al. ............. 250/339.09 |
| 6,146,897 | * | 11/2000 | Cohenford et al. .................... 436/63 |

OTHER PUBLICATIONS

Wood, B. FTIR Microspectroscopic Study of Cell Types and Potential Confounding Variables in Screening for Cervical Malignancies. Biospectroscopy 4(2)75–91, Feb. 1998.*

Hook, G.R. et al., (1986), "A sample preparation for quantitative determination of magnesium in individual lymphocytes by electron probe X–ray microanalysis", Journal of Microscopy, vol. 141, Pt 1.

Shim, M.G. et al., (1996), "The Effects of ex vivo Handling Procedures on the Near–Infrared Raman Spectra of Normal Mammalian Tissues", Photochemistry and Photobiology, 63(5), pp. 662–671.

* cited by examiner

Primary Examiner—Ralph Gitomer

(57) ABSTRACT

Tissue cells are preserved for infrared spectroscopic analysis by soaking a fresh cellular specimen in a 0.5 to 3.0% concentration inorganic salt solution, removing excess salt solution by centrifuging, placing the remaining damp specimen on an infrared optical window and then drying the specimen in a flow of room temperature air such that a dried, spectrally preserved specimen is obtained within 2 minutes. Alternatively, a cellular specimen in wet and fresh form is placed on the surface of a crystal water-soluble inorganic salt in the form of an infrared window to dissolve some of the salt and thereby cover the specimen with the dissolved salt solution and then drying the specimen as described above in less than 2 minutes. In both cases, the drying results in the formation of a salt crystal film covering the surface of the cells for spectral preservation. Another feature is an infrared spectroscopic method in which polymorph effects are avoided by obtaining an infrared spectrum of pure polymorph cells and subtracting this from superimposed infrared spectra of tissue cells and polymorphs.

13 Claims, 8 Drawing Sheets

METHOD OF PRESERVING BIOLOGICAL TISSUE SPECIMENS AND METHOD OF INFRARED SPECTROSCOPIC ANALYSIS WHICH AVOIDS THE EFFECTS OF POLYMORPHS

BACKGROUND OF THE INVENTION

The present invention relates to methods for preserving biological tissue specimens to be subject to infrared spectroscopy for detecting a malignant or premalignant anomaly, and for removing the effects of polymorphs for infrared spectroscopic detection of cellular anomalies.

It has been well documented that infrared spectra of various human cancers and precancerous lesions differ substantially from those of the corresponding normal tissues and cells. Several attempts have been made to develop infrared spectroscopic methods for the screening of cytological anomalies, in particular the screening of cervical malignancy or premalignant anomalies. The commonly used cytological screening methods, such as the Pap smear test, are mainly based on the morphological changes of cells, whereas the infrared spectroscopic method is based on the structural changes at the molecular level in cells. Since structural changes at the molecular level occur before morphological changes in abnormal cells, the infrared spectroscopic method is expected to be more accurate than the conventional cytology method in terms of early detection of malignant and premalignant anomalies. A recent clinical study (Ref. 11) has shown that the false negative rate of the infrared spectroscopic method for the screening of the neoplastic cervical cells is about ten times better than the traditional Pap smear test. However, there are still two main obstacles in the infrared spectroscopic method, which cause an extremely high false positive rate and prevent the infrared spectroscopic method from being acceptable for routine cytological screening. These two obstacles relate to problems caused by polymorph effects and in sample preparation.

In many areas of the world, the majority of the cervical specimens exhibit positive results when the infrared spectroscopic method is used. After many years research, we found that this extremely high false positive rate was essentially due to the effects of polymorphs. When a cervical specimen exhibits mild to moderate inflammation, the changes in the molecular arrangement and structure in the cells are insignificant but a considerable amount of polymorph cells are present in the cervical specimen. The presence of a large amount of polymorphs in the cervical cell specimen not only prevents the search for abnormal cervical cells in the specimens under a microscope by the conventional Pap smear test, but also prevents the infrared spectroscopic method from distinguishing a normal cervical specimen from an abnormal one. When polymorphs are present in a cervical specimen, the resulting infrared spectrum is a superimposed spectrum composed of the infrared spectra of cervical cells and polymorph cells. The infrared spectrum of polymorph cells has many features similar to those in the infrared spectra of various precancerous and atypical cells. Consequently, in the presence of polymorphs, a non-neoplastic cervical cell specimen will show an infrared spectrum similar to that of the precancerous or atypia cervical cells, which will lead to a false positive diagnosis.

In many areas of the world, cervical specimens with mild to moderate inflammation are very common place due to the specific environmental effects and sexual behavior in these areas. Therefore, a majority of the cervical specimens from the general public in these areas are accompanied with a significant amount of polymorphs. Consequently, the infrared spectroscopic method may lead to a false positive diagnosis for a majority of the population. This false positive effect of polymorphs must be removed before the infrared spectroscopic method can be adopted to the screening of cervical anomalies for the general population.

Another obstacle in the infrared spectroscopic method is problems in the sample preparation. At the present time, there are several methods to prepare cellular samples for infrared spectroscopic study.

The most common method is the wet process. In this process, exfoliated fresh cells are suspended in saline, centrifuged into a cellular pellet, and some of the wet pellet is then placed on an infrared spectroscopic sample holder for the infrared spectroscopic measurement and analysis.

Benedetti et al., G. Appli. Spectrosc., 44: 1276–1280 (1990) have adopted a method of infrared spectroscopic study for powdered solid samples in which they prepared dry solid powder of fresh biological cells for infrared spectroscopic analysis. In this dry process, fresh lymphocytes were separated from other constituents in the blood by chemicals, and the fresh lymphocytes were dried into a solid. The solid lymphocytes were ground into fine powder with KBr powder. The mixture of solid lymphocyte and KBr was then pressed into a clear solid pellet for infrared spectroscopic analysis. The infrared spectroscopic results obtained by this process are usually inaccurate due to the fact that grinding destroys the cellular form of lymphocytes, creating structural changes at the molecular level which mask those arising from neoplasm and other diseases, and decompose some biomolecules in the cells by the heat generated from the grinding.

In the dry process described by Gal et al., Anticancer Research, 14: 1541–1548 (1994), fresh cultured cells were washed and suspended in normal saline, smeared on a ZnSe window, evaporated for 10 minutes at 37° C. and then the infrared spectrum of the exposed cellular proteins was measured. It is evident from Example 1 that in this process, the intermolecular structure in the cells was destroyed by the hypertonic crenation during the heating and drying process and thus no infrared spectrum of most of the important cellular molecules could be obtained. Only the infrared spectra of the exposed cellular proteins could be measured.

All the present wet and dry sample preparation methods for infrared spectroscopic study of tissue cells are dealing with fresh cells without any preservation. If the fresh cell specimens are not used immediately for infrared spectroscopic analysis, for instance cellular specimens are transported to the pathology laboratory before they are prepared for infrared spectroscopic analysis, the fresh cell specimens must be kept frozen until they are ready for analysis. At room temperature, cellular specimens either in the fresh form or in saline solution will deteriorate very fast. The infrared spectra of deteriorating cells have features similar to those in the spectra of abnormal cells and will lead to a false diagnosis and an increase in the false positive rate.

In many countries, screening of cervical anomalies is done in central laboratories. The transportation of the cervical specimens from the clinics to the central laboratory in the frozen form is extremely impractical. Moreover, in common practices, the cervical cell specimens after preparation are required to be kept for several years for future references in hospitals and clinics. One way to keep the cervical specimens for several years is to store the specimens in a liquid nitrogen tank. For a large number of specimens, such as cervical specimens for screening, to keep the specimens in liquid nitrogen is extremely impractical. The best way to resolve these problems is to fix cellular specimens by preservatives.

The criteria for the selection of preservatives and methods of preservative treatment, which are suitable for the detection of anomalies in tissue cells by infrared spectroscopic technology, are as follows: (1) The preservative must not have any chemical reaction with biomolecules in tissue cells to cause structural changes at the molecular level; (2) The preservative treatment must not damage the intermolecular arrangement and intramolecular structure in cells, which are the basis of detection of anomalies in cells by the infrared spectroscopic method; and (3) The preservative must not have infrared absorption bands at the same frequency regions as the infrared absorption bands of biological tissue cells. Otherwise, the infrared spectra of tissue cells are masked by the infrared spectra of the preservatives, which makes the analysis of the infrared spectra of cells to detect cellular anomalies impossible. Unfortunately, all the conventional preservatives (or fixatives) for biological tissues and cells in pathology and cytology, such as alcohol, formalin, nitrates, etc. do not meet these criteria.

In Hook et al., J. Microscopy, 141: 69–78 (1985) cell samples were prepared for the determination of the amount of magnesium ion in cells. The cells were suspended in an ammonium nitrate solution or buffered saline glucose solution, deposited on the analysis support and then air dried. This sample preparation method can not be adopted for the infrared spectroscopic method because both ammonium nitrate and glucose strongly interact with cellular molecules and cause molecular rearrangement and structural changes in tissue cells. Moreover, both ammonium nitrate and glucose have infrared absorption bands in the frequency regions of the infrared absorption bands of tissue cells and thus interfere with the spectral analysis of cells. Hook et al. were only interested in the determination of the amount of magnesium ion in cells. Therefore, either the damage of the cellular structural or interactions of cellular molecules with preservatives and other molecules in the sample preparation were not their concern.

In Sinor et al., U.S. Pat. No. 5,030,560, issued Jul. 9, 1991, cells were preserved with a drying solution consisting of monosaccharide, disaccharide, trisaccharide or cyclitol and a salt. In their sample preparation method, the washed cells must be deposited onto a dye coated solid-phase support in the form of a monolayer of cells. Then, the drying solution was added to the surface of the solid-phase support containing the cell monolayer. After a period of incubation, the excess drying solution was removed from the cell monolayer. Finally, the remaining drying solution was absorbed by the dessicant material in a sealed container for 3–8 days at 2–8° C. Cells were lysed before the application of the drying solution, which allowed the drying solution better access to the inside of the cells. Saccharides and cyclitol in their drying solution strongly interact with cellular molecules and change the structure and arrangement of cellular molecules. Saccharides and cyclitol also have strong absorption bands in the infrared frequency regions of the absorption bands of biological tissues and cells. The lysis procedure in this method also changes the molecular structure and arrangement in cells. Therefore, this drying solution is not suitable for the infrared spectroscopic study of biological cells. The interaction of saccharides with cellular molecules and the changes of intermolecular structures in the cells were not the concerns of Sinor and Eatz because their cell preparation was for immunoassays which takes place on the surface of cells. Moreover, the drying process in the Sinor et al. procedure is too tedious and not practical for a routine screening of cervical specimens by the infrared spectroscopic method.

It is an object of the present invention to provide a simple and effective method for the infrared spectral preservation of tissue cells for infrared spectroscopic analysis.

It is a further object to spectrally preserve the tissue cells such that they can be safely stored for years at room temperatures.

It is a still further object of the invention to provide a process to remove the polymorph effects from the infrared spectra of negative specimens in order to reduce the false positive rate to such a level that the use of the infrared spectroscopic method for the screening of cellular anomalies becomes practically possible.

SUMMARY OF THE INVENTION

According to one embodiment of the invention, a method has been developed for preserving tissue cells for infrared spectroscopic analysis by combining a special drying process and treatment by a salt solution. A fresh cellular specimen is soaked in an inorganic salt solution having a salt concentration in the range of about 0.5 to 3.0% by weight. The excess salt solution is removed from the specimen by centrifuge. The damp specimen with some remaining salt solution is placed on an infrared optical window and then the water in the specimen on the window is evaporated by a forced air at room temperature such that a dried, spectrally preserved specimen for infrared spectroscopic analysis is obtained within a drying time of no more than about 2 minutes. The time for the evaporation is critical in this process. The specimens must be dried before the hypertonic crenation of the cells in the wet form takes place. Also, the drying time must be controlled such that the dried salt will be in the form of crystal film covering the surface of the cells. If the specimens are dried too fast, for instance by vacuum or freeze dry, then the recrystalized solid salt will be in a fine powder form. These fine salt powders will cause a scattering of the infrared light, resulting in a poor spectrum which makes the spectral analysis impossible. Thus, a drying time within the range of about 1–2 minutes is preferred. The specimens must be dried at room temperature without heating to avoid the degradation of cells. The inorganic salts are, but not limited to, sodium chloride, sodium bromide, potassium chloride and potassium bromide.

According to a further embodiment of the invention, a cellular specimen in wet and fresh form characteristic of that freshly removed from a living body, is placed on the surface of a crystal of water-soluble inorganic salt in the form of an infrared optical window. The moisture from the wet specimen dissolves some of the salt crystal and thus the specimen is cover with the dissolved salt solution. The specimen on the crystal is then dried with force air at room temperature such as to obtain a dried, spectrally preserved specimen within a drying time of no more than about 2 minutes, preferably about 1–2 minutes. The drying time and process are control to such that no hypertonic crenation or degradation of the cells will take place and the recrystalized salt will be in the form of crystal film covering the surface of the cells. The crystal of water soluble inorganic salts are, but not limited to, sodium chloride, sodium bromide, potassium chloride and potassium bromide crystal.

An essential feature of both of the above procedures is the manner of drying, i.e., the specimen coated with salt solution is quickly dried such that a crystal film is covering the surface of the cells. At this point no free moisture remains and a dry, preserved specimen has been obtained. Specimens preserved in this way have substantially maintained their spectral characteristics for more than three years.

The present invention also includes a method for removing the polymorph effects from the infrared spectra of negative specimens in order to reduce the false positive rate to such a level that the use of the infrared spectroscopic method for the screening of cellular anomalies becomes practically possible. This is achieved by obtaining an infrared spectrum of pure polymorphs. Then the infrared spectrum of the pure polymorph cells is subtracted from the superimposed infrared spectra of tissue cells and polymorphs, e.g. by digital subtraction.

DESCRIPTION OF THE PREFERRED EMBODIMENTS

In this specification, fresh biological tissue or cells in natural or cultured form means biological tissue or cells newly obtained, cultured tissue or cells, or cells exfoliated from fresh biological tissues which are substantially free of degradation by exposure to room temperature. A typical room temperature is in the range of about 15–28° C.

The specimens may be prepared from fresh microtome sections of tissue biopsy, punched or needle tissue biopsy, cultured cells or exfoliated cells. Typical of the exfoliated cells are Papanicolaou smears, cervical specimens, endocervical specimens, ectocervical specimens, vaginal specimens, uterus specimens or bronchial specimens.

A typical tissue may be liver tissue, and the anomaly an indication of malignancy in the liver tissue. Typical cells may be ovarian epithelial cells. When the specimen is tissue, the tissue may be cervical tumor tissue and the anomaly an indication of malignancy in the tissue. When the specimen is exfoliated cells, the specimen may be obtained from scraping, brushing, washing, secretions, exudates or transudates from various organs and tissues.

Figure 15:
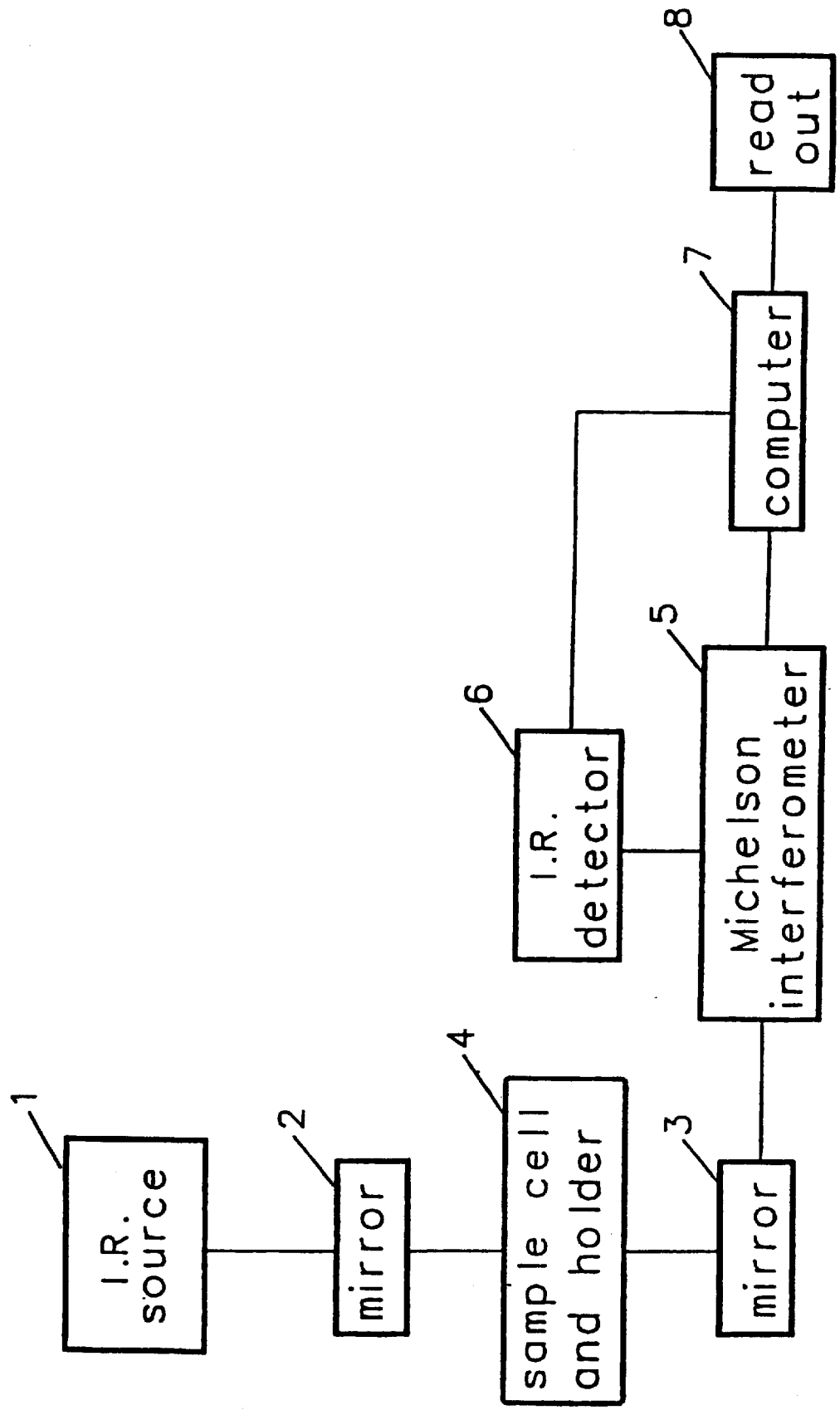
FIG. 15 is a block diagram of an apparatus for detecting the presence of anomalies in biological specimens using infrared spectroscopy.

A typical apparatus for conducting the infrared spectral analyses is shown in FIG. 15. It includes an infrared source 1, infrared beam focusing mirrors 2 and 3, a sample cell and holder 4, a Michelson interferometer 5, a infrared light detector 6, a computer 7, and a readout 8. In the following tests, the infrared source L, infrared beam focusing mirrors 2 and 3, the holder of the sample cell and holder 4, Michelson interferometer 5, and infrared light detector 6 were components of a Nicolet Magna IR 550 Fourier-transform infrared spectrometer obtainable from Thermo Instruments (Canada) Inc., Mississauga, Ontario, Canada. The sample cell of the sample cell and holder 4 for measuring the transmission infrared spectra had a single infrared optical window on which the specimen was deposited or two infrared optical windows between which the specimen was placed. The sample cell of the sample cell and holder 4 for measuring ATR infrared spectra was a contact SamplerTM ATR accessory (Spectra-Tech, Inc.) with a ZnSe crystal, obtained from Spectra-Tech, Inc., Stamford, Connecticut.

In operation, a biological tissue or cell sample was placed in a transmission or ATR sample cell of the sample cell and holder 4, a beam of infrared light from the source 1, which had been condensed by the focusing mirror 2, was passed through the sample in the sample cell and holder 4 and was focused to the detector 6 through Michelson interferometer 5 by the focusing mirror 3. Any infrared absorption by an anomaly in the specimen was detected by the Michelson interferometer 5 and the detector 6, which, in turn, was computed by the computer 7 to give a readout at the readout 8. The computer readout may be programmed for the readout 8 to directly indicate whether the sample is a normal healthy one or one which contains an anomaly, which may be, for example, benign, dysplasia, or malignant.

In a typical procedure for obtaining fresh, exfoliated cervical cells, a cervical specimen diagnosed as normal and healthy was obtained from a patient by exfoliation with a spatula. Within one-two minutes, the spatula containing the specimen was immersed in a centrifuge tube containing an aqueous solution of about 0.9%–1.0% sodium chloride (by weight). Prior to immersion, the specimen was in a generally wet, fresh-specimen from characteristic of exfoliated cells that had been freshly removed from a living body. The volume of the aqueous saline solution was about 10 ml. The weight of specimen material was about 40 mg.

Immediately after immersion, the sample was vortexed to transfer the exfoliated cervical cells from the spatula into the saline solution. After the spatula was removed from the centrifuge tube, the sample was centrifuged for about 4 min. at about 4000 rmp in a standard biological centrifuge unit (model Centra CL2, available from International Equipment Company, Mass.). The supernatant, excess NaCl solution, was decanted leaving the specimen, soaked with NaCl solution, at the bottom of the centrifuge tube.

EXAMPLE 1

Figure 1:
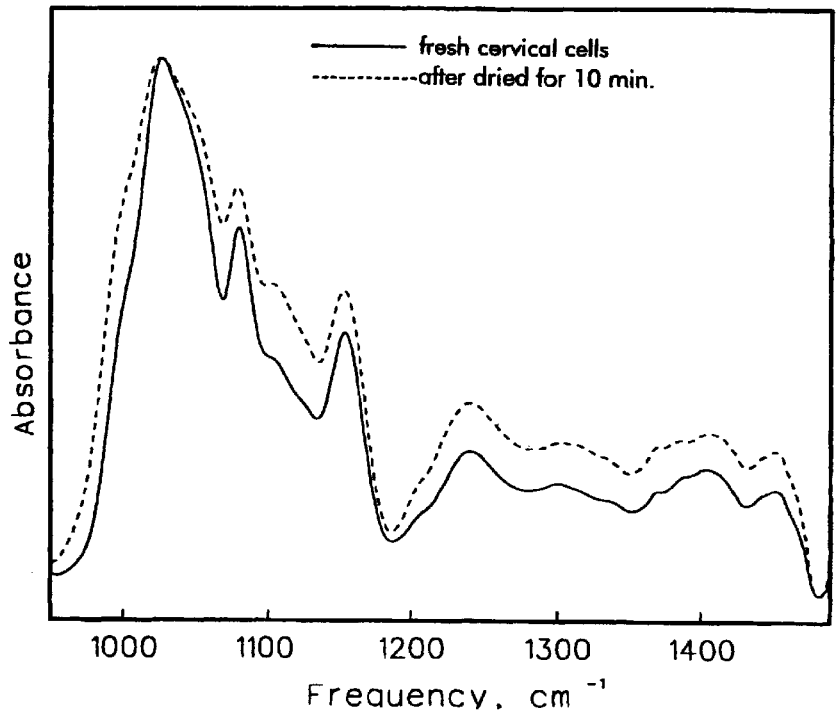
FIG. 1 shows an infrared spectra in the frequency region 950 to 1500 $cm^{-1}$ obtained from a fresh, normal healthy, exfoliated cervical cells and after air drying the specimen at 28° C. for 10 minutes.

A fresh, normal healthy cervical cell specimen was obtained from a patient by exfoliation with a spatula. This was collected by immersion in an aqueous saline solution and centrifuging to obtain a damp saline cell pellet. A portion of the pellet was placed on a silicon infrared window and immediately subjected to infrared spectral analysis. A further portion of the pellet was allowed to sit at 28° C. to air dry for 10 minutes, after which it was also subjected to infrared spectral analysis. FIG. 1 shows the infrared spectra in the 950 to 1490 $cm^{-1}$ region of the above two specimens. A substantial difference can be seen in the absorption bands due to the hypertonic crenation and degradation of the cells during the long drying and heating process.

EXAMPLE 2

Figure 2:
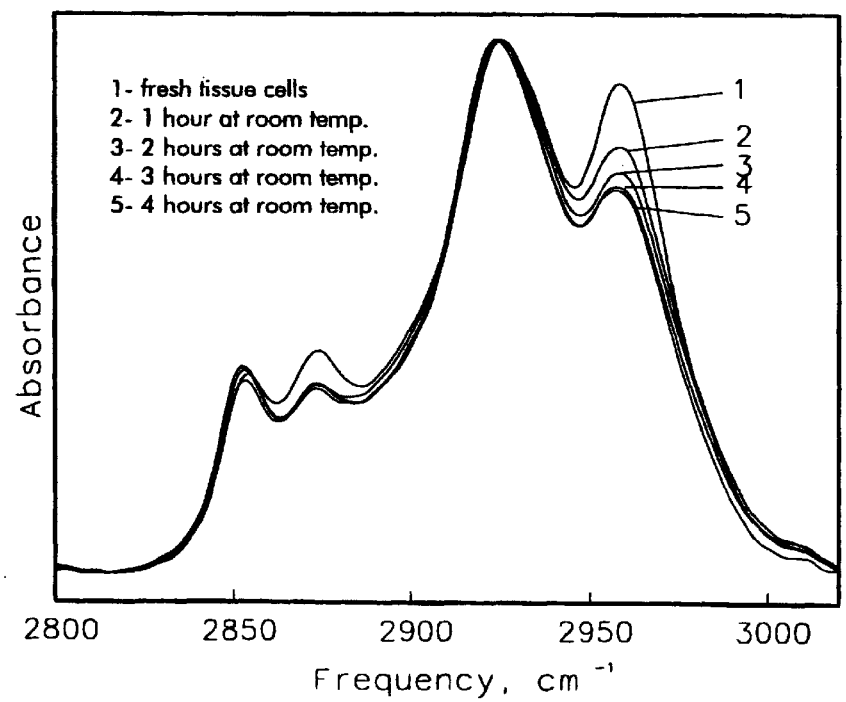
FIG. 2 shows an infrared spectra in the frequency region 2800 to 3020 $cm^{-1}$ obtained from a fresh, normal health, liver tissue cell specimen that was not treated with a preservative and after keeping the specimen at room temperature and measured after the passage of various time periods.
Figure 3:
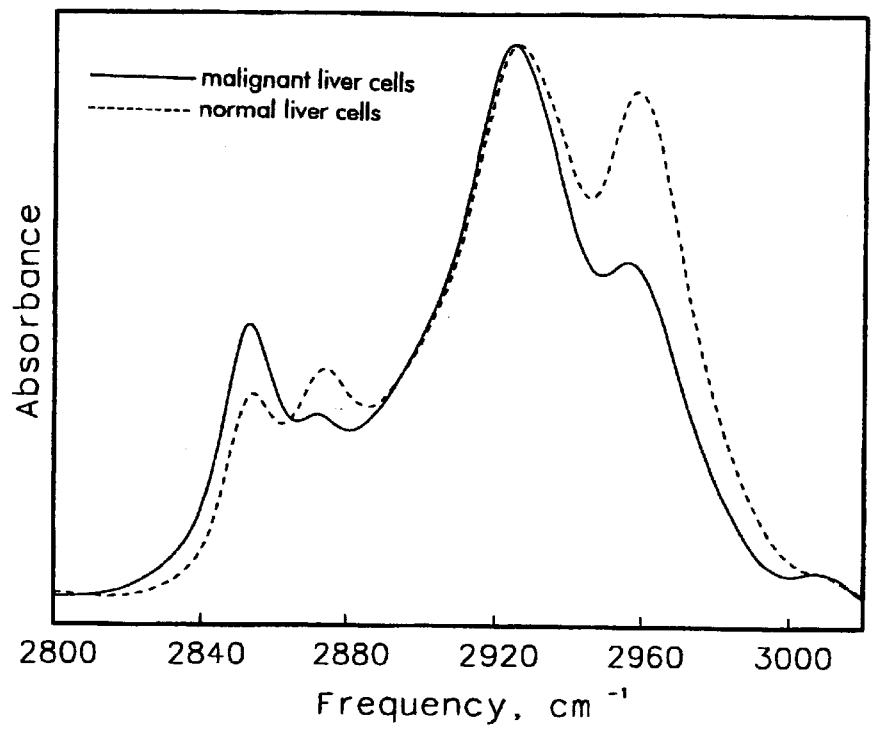
FIG. 3 shows a similar infrared spectra to that shown in FIG. 2, but for normal healthy and malignant specimens.

A fresh, normal healthy liver cell specimen was obtained and tested for deterioration when left for a period of time at room temperature. FIG. 2 shows the infrared spectra in the 2800 to 3000 $cm^{-1}$ range of the fresh, normal healthy liver cell specimen, and after keeping the specimen at room temperature for various periods of time (spectrum 1 is from fresh, normal healthy tissue cell specimen; and spectra 2, 3, 4, 5, designate the infrared spectra for the same specimen kept at room temperature for 1, 2, 3, and 4 hours, respectively). The infrared spectrum of the fresh, normal healthy liver cell specimen kept at room temperature for 4 hours is similar to that of a malignant liver cell specimen as shown in FIG. 3. These spectra have demonstrated that the infrared spectra of deteriorated cells will give a false positive diagnosis.

EXAMPLE 3

Figure 4:
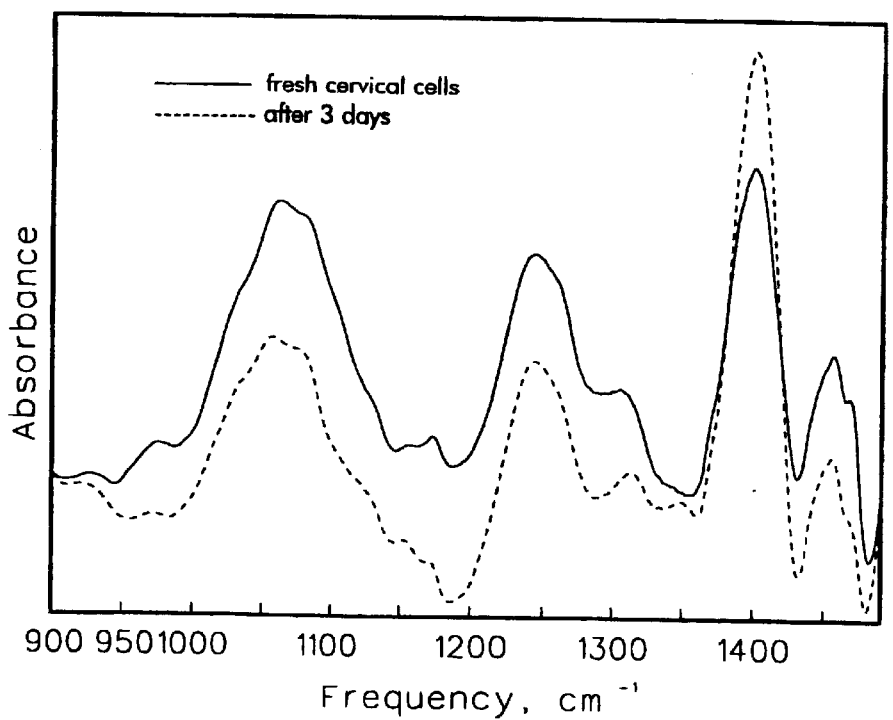
FIG. 4 shows an infrared spectra in the frequency region 900 to 1500 $cm^{-1}$ obtained from a specimen of fresh, exfoliated cervical cells which was diagnosed as high grade dysplasia and after keeping the specimen at room temperature for three days in saline.
Figure 5:
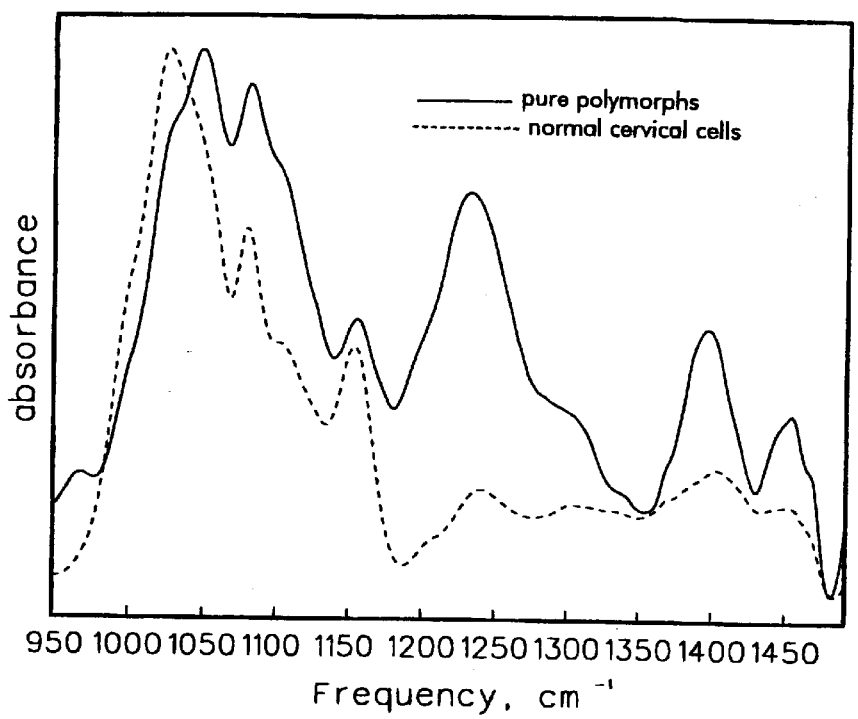
FIG. 5 shows an infrared spectra in the frequency region 950 to 1500 $cm^{-1}$ obtained from a specimen of fresh, normal, exfoliated cervical cells and a specimen of pure polymorphs isolated from human blood.

For this test, fresh, exfoliated cervical cells were obtained which had been diagnosed as high grade dysplasia. FIG. 4 shows infrared spectra in the frequency region 900 to 1500 $cm^{-1}$ obtained from these fresh, exfoliated cervical cells, and after keeping the specimen in saline (0.9% NaCl) at room temperature for three days. It is evident from FIG. 4 that after the cervical cell specimen was kept in saline at room temperature for three days, the shape, frequency and intensity of various absorption bands in the entire spectrum were changed dramatically, which indicated that the cervical cells had deteriorated dramatically and cervical cells in a 0.9% NaCl solution without a drying process are not preserved.

EXAMPLE 4

The purpose of this test was to compare the infrared spectrum of pure polymorphs and a normal cervical specimen. The pure polymorphs were extracted from the blood of the patient. The infrared spectrum of pure polymorph cells is characteristic of strong absorption of the nucleic acid band near 1240 $cm^{-1}$ and weak absorption of the C-OH band and the glycogen band at 1155 $cm^{-1}$ and 1025 $cm^{-1}$, respectively. The infrared spectrum of normal cervical cells is opposite to that of the polymorphs with strong intensities of the 1155 $cm^{-1}$ and 1025 $cm^{-1}$ bands and weak intensity of the 1240 $cm^{-1}$ band.

EXAMPLE 5

Figure 6:
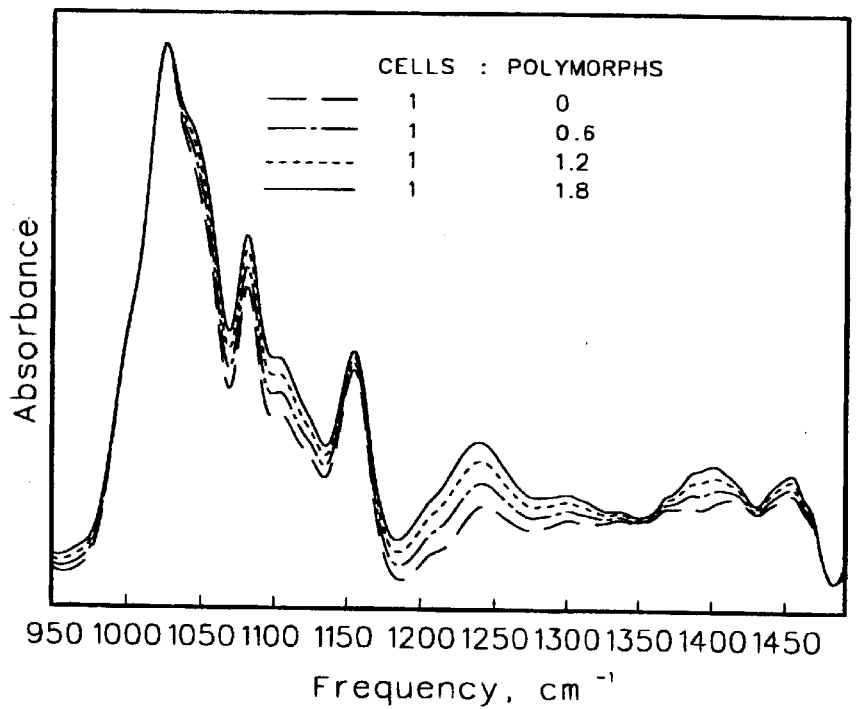
FIG. 6 shows an additional infrared spectra in the frequency region 950 to 1500 $cm^{-1}$ obtained from the addition of the spectrum of a specimen of fresh, normal, exfoliated cervical cells and the spectrum of pure polymorphs with various ratios between the cervical cells and polymorphs.

This example shows the removal of polymorph effects on the infrared spectroscopic screening method. A combination of an infrared spectrum of normal cervical cells with various ratios of the infrared spectrum of polymorphs is illustrated in FIG. 6. The combination of an infrared spectrum of normal cervical cells with an infrared spectrum of pure polymorphs give rise to an intensity increase in the 1240 $cm^{-1}$ band and an intensity decrease in the 1155 and 1025 $cm^{-1}$ bands. These resulting infrared spectra in FIG. 6 are comparable with those of various precancerous cervical cells and lead to a false positive diagnosis. To remove the polymorph effects on the infrared spectroscopic screening method, the infrared absorption of polymorphs in the infrared spectra of cervical cells are removed by a digital subtraction of the infrared spectrum of pure polymorph cells from the superimposed infrared spectra of tissue cells and polymorphs. The subtraction is performed stepwise with increasing scales of the infrared spectrum of polymorphs until the intensity of the 1240 $cm^{-1}$ band reaches the intensity level of normal cervical cells. Then inspection is made for the spectral parameters of other regions of the spectrum. If the spectral parameters of the other regions of the spectrum after subtraction are comparable with those of normal cervical cells, then the diagnosis of this cervical specimen is negative from neoplasm. On the other hand, if the infrared spectral parameters and absorption intensities of other regions of the spectrum after subtraction are higher or lower than those of normal cervical cells, then the diagnosis of the specimen is abnormal (neoplasm). All these subtraction, calculation and comparison can be performed automatically by building all these features into a software. A test of this process for a groups of 650 cervical specimens in a general population has shown that the false positive rate was reduced from 516 to 4.1% after the polymorph effects were removed.

EXAMPLE 6

Figure 7:
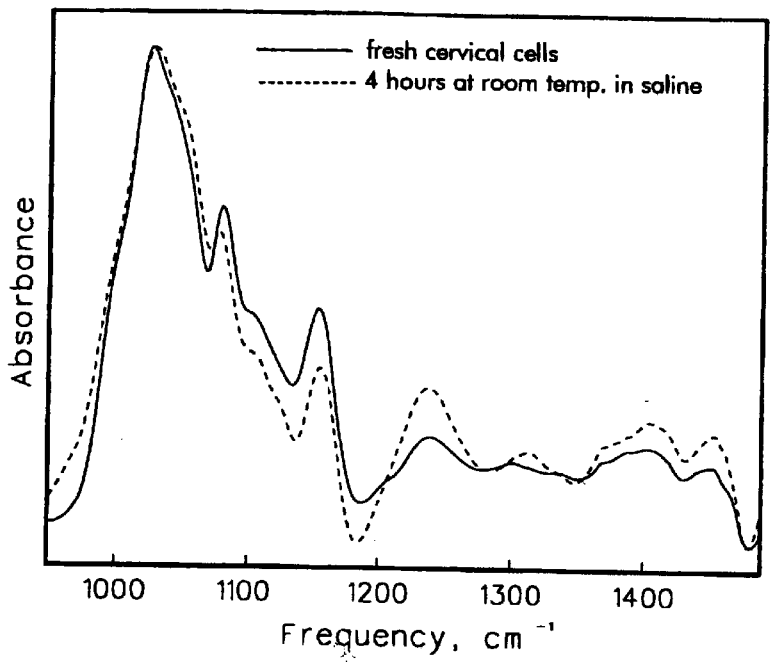
FIG. 7 shows an infrared spectra in the frequency region 950 to 1500 $cm^{-1}$ obtained from a specimen of fresh, normal, exfoliated cervical cells and after keeping the specimen at room temperature for four hours in 1% NaCl solution.

Tests were conducted to determine the effect of a 1% sodium chloride solution on normal cervical cells. The infrared spectrum of normal cervical cells was recorded immediately after freshly removing from a living body and placing in wet pellet form and this was compared with the infrared spectrum of the same normal cervical cells after they were suspended in a 1% sodium chloride solution for 4 hours at room temperature. The results are shown in FIG. 7. The spectrum of the normal cervical cells after they were suspended in 1% sodium chloride without the specific drying process for four hours changed dramatically and is similar to the infrared spectra of abnormal cervical cells. This change in the infrared spectrum indicates that 1% sodium chloride contains insufficient sodium chloride to preserve the normal cells and the cells in 1% sodium chloride solution are deteriorated in 4 hours at room temperature. If a salt solution of a very high concentration is used, it may preserve the cells from deterioration. However, it is well known that in a salt solution of a high concentration, biological cells undergo hypertonic crenation, which results in dramatically changes in the molecular arrangement and structure in cells. These changes will certainly alter the infrared spectrum from that of normal cells.

EXAMPLE 7

Figure 8:
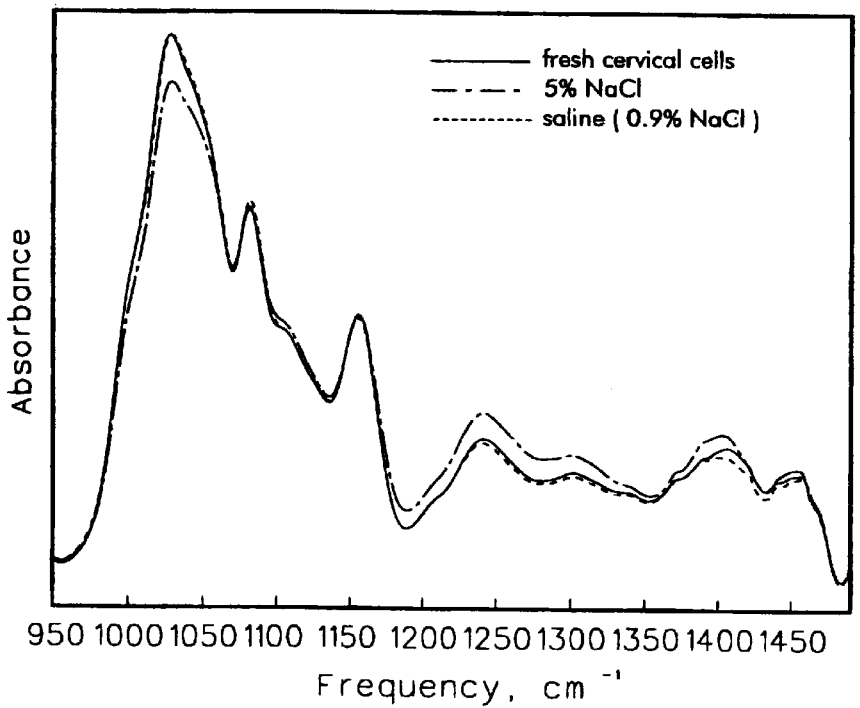
FIG. 8 shows an infrared spectra in this frequency region 950 to 1500 $cm^{-1}$ obtained from a fresh, normal cervical cell specimen and immediately after suspending the specimen in 5% NaCl solution, or saline.

A further test was conducted to determine the effect of salt solutions having other concentrations. For this test a specimen of fresh, normal cervical cells was obtained in wet pellet form. Part of the specimen was immediately subjected to infrared spectral analysis. Also a portion was suspended in 5% sodium chloride solution and a further portion was suspended in saline solution (0.9% NaCl) and these were also immediately subjected to infrared spectral analysis. FIG. 8 shows the infrared spectrum obtained from a specimen of fresh and normal cervical cells in the wet pellet form, and immediately after the cell specimen was suspended in 5% sodium chloride solution, or saline solution. It is evident that the cervical cells were damaged after the treatment of 5% sodium chloride and the infrared spectrum of this treated cells changed into a spectrum similar to that of abnormal cells.

EXAMPLE 8

Figure 9:
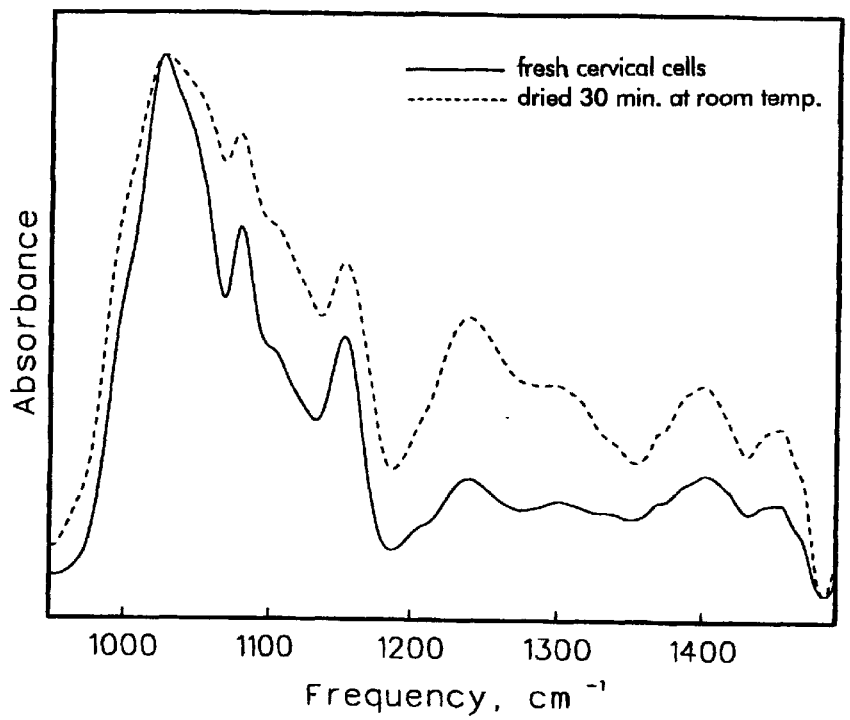
FIG. 9 shows an infrared spectra in the frequency region 950 to 1500 $cm^{-1}$ obtained from a fresh, normal cervical cell specimen and after air drying for 30 minutes at room temperature.

When the water in a salt solution with suspended tissue cells is evaporated, salt will crystallized and form a solid film on the dried cells. In this case, the cells will certainly be preserved but whether the molecular arrangement and structure in cells are modified by this treatment is unknown. FIG. 9 shows the infrared spectra of a fresh, normal cervical cell specimen and the same specimen after the specimen was suspended in a 1% sodium chloride solution, centrifuged into pellet and left at room temperature to evaporate its water content for 30 minutes. The infrared spectrum of the cervical cell specimen changed considerably after the cell specimen was treated by 1% sodium chloride and slowly evaporated at room temperature for 30 minutes. The resulting infrared spectrum is similar to the infrared spectrum of a wet pellet of abnormal cervical cells. This result has demonstrated that the drying time for the cervical cell specimen in the 1% sodium chloride was too long. During the drying process the concentration of the sodium chloride solution is increased gradually from 1%. While the cells were still in the wet form, the concentration of the sodium chloride has already increased to such a level to cause the hypertonic crenation of the cells, which resulted in a dramatically change in the molecular arrangement and structure in cells and thus in the infrared spectrum.

EXAMPLE 9

Figure 10:
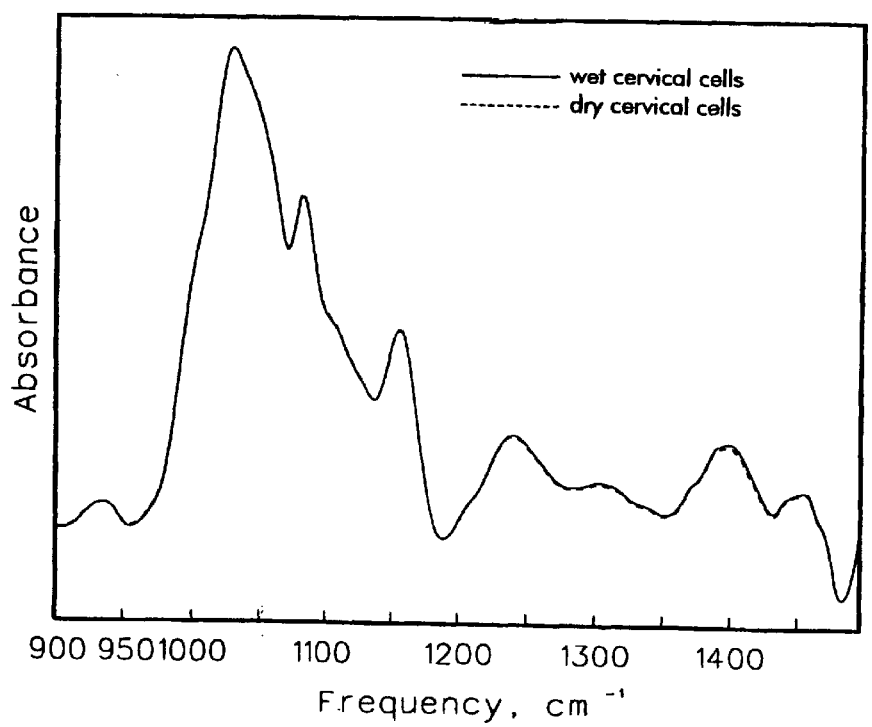
FIG. 10 shows an infrared spectra in the frequency region 900 to 1500 $cm^{-1}$ obtained from a 1% NaCl solution treated wet specimen of fresh, normal healthy, exfoliated cervical cells and after the wet specimen was air dried at room temperature on a sample holder for two minutes.

In order to apply the spectral preservative procedure for the screening of cellular anomalies, the molecular arrangement and structure in the preservative treated and dried cells must not be changed from those of the wet fresh cells. FIG. 10 shows the infrared spectrum of a wet specimen of fresh, normal, healthy, exfoliated cervical cells in wet pellet form and the infrared spectrum of the same specimen after it was spectral preservative treated and dried on an infrared optical window with the procedure described above. It is evident from FIG. 10 that there is substantially no change in the infrared spectrum for the specimen after it was spectrally preserved by air drying at room temperature for 1–2 minutes from that of the wet fresh cells.

EXAMPLE 10

Figure 11:
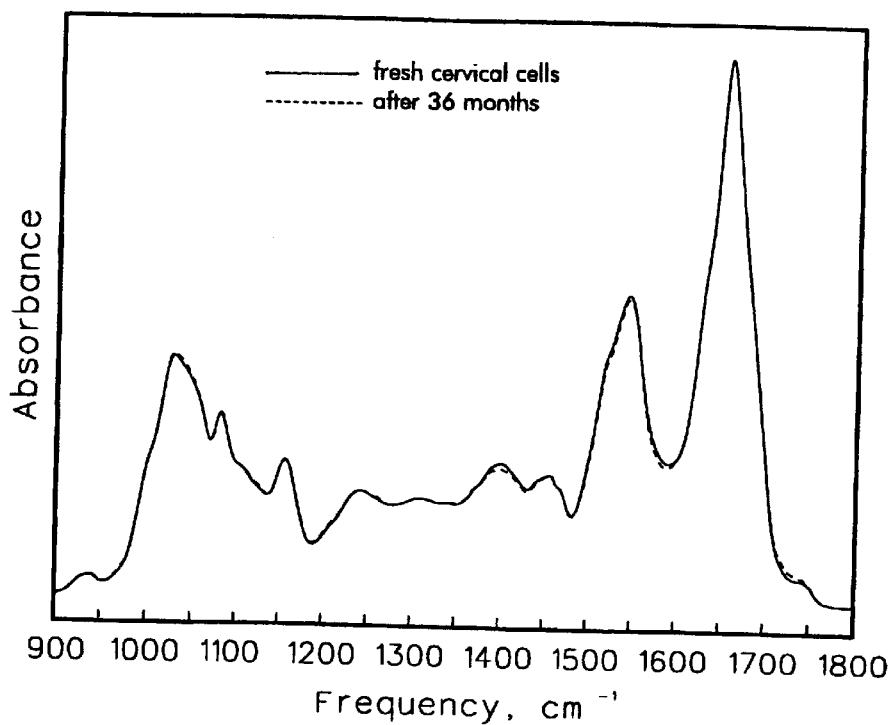
FIG. 11 shows an infrared spectra in the frequency region 900 to 1800 $cm^{-1}$ obtained from a preservative treated and air dried specimen of fresh, normal, healthy, exfoliated cervical cells and after keeping the specimen at room temperature for thirty six months.

A specimen of fresh, normal healthy, exfoliated cervical cells was obtained and suspended in 1% sodium chloride solution, then centrifuged to remove excess fluid leaving a damp specimen. Portion of the damp sample was placed on a silicon infrared window and this was placed in a stream of room temperature air for 1–2 minutes resulting in the drying of the specimen and the formation of a crystal film covering the surface of the cells. This spectrally preserved specimen was subjected to immediate infrared spectral analysis and was kept at room temperature for 36 months after which it was subjected to infrared spectral analysis. FIG. 11 shows the infrared spectra that were obtained in the frequency region 900 to 1800 $cm^{-1}$ from the spectral preservative (1% aqueous solution of sodium chloride) treated and 1–2 minutes air dried specimen of fresh, normal healthy, exfoliated cervical cells, and after keeping the dried specimen at room temperature for 36 months. It is evidence from FIG. 11 that there is substantially no change in the spectrum for the spectrally preserved specimen over the period of three years at room temperature.

EXAMPLE 11

Figure 12:
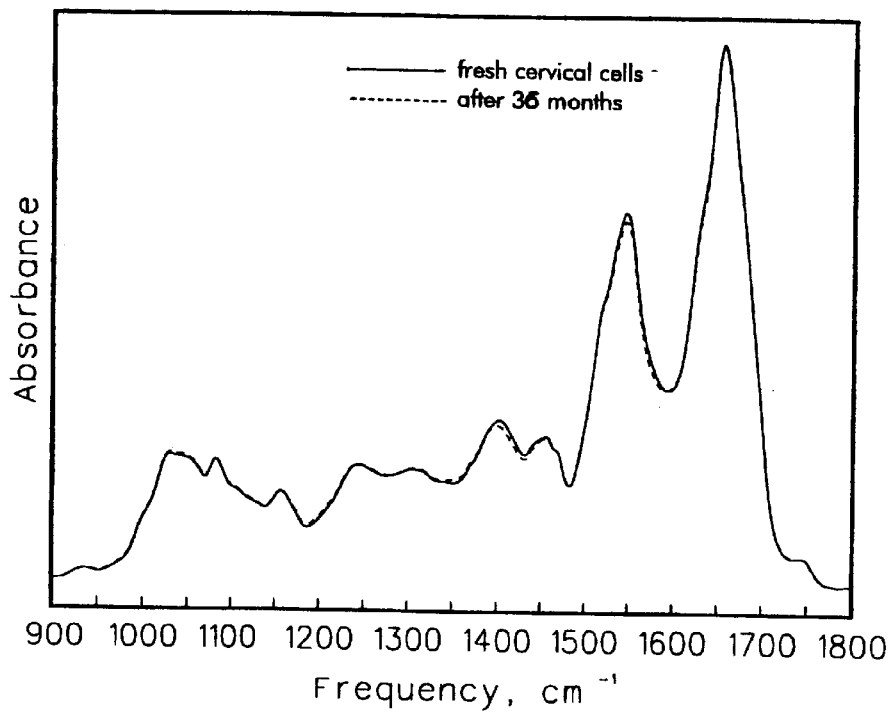
FIG. 12 shows an infrared spectra in the frequency region 900 to 1800 $cm^{-1}$ obtained from a preservative treated and air dried specimen of fresh, exfoliated cervical cells which has been diagnosed as low grade dysplasia, and after keeping the specimen at room temperature for thirty six months.

The same procedure was followed as in Example 10, except that the specimen was fresh, exfoliated cervical cells diagnosed as having low grade dysplasia (CIN 1). FIG. 12 shows the infrared spectra that were obtained in the frequency region 900 to 1800 $cm^{-1}$ from a spectral preservative treated and dried specimen of fresh, exfoliated cervical cells diagnosed as having low grade dysplasia (CIN 1), and after keeping the specimen for 36 months at room temperature. It is evident from FIG. 12 that there is substantially no change in the spectra for the treated specimen over the period of three years at room temperature.

EXAMPLE 12

Figure 13:
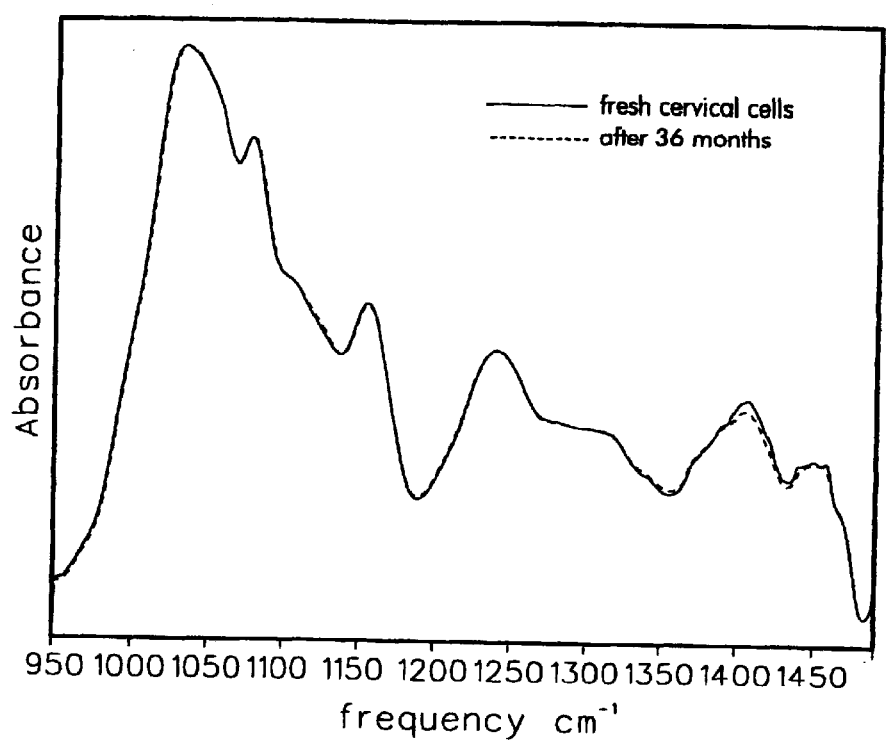
FIG. 13 shows an infrared spectra in the frequency region 950 to 1500 $cm^{-1}$ obtained from a preservative treated specimen (by the second method) of fresh, exfoliated cervical cells which has been diagnosed as moderate dysplasia, and after keeping the specimen at room temperature for thirty six months.

A specimen of fresh, exfoliated cervical cells diagnosed as having moderate dyplasia (CIN II) was obtained. For this test. The wet specimen was placed on the surface of a water-soluble KBr crystal in the form of an infrared optical window and was dried in a stream of room temperature air for less than 2 minutes to obtain a dry sample with a crystal film covering the surface of the cells. FIG. 13 shows the infrared spectrum in the frequency range 950 to 1500 $cm^{-1}$ obtained from a preservative treated specimen by this second spectral preservative treatment process and the infrared spectrum of the same specimen after keeping the preservative treated specimen for 36 months at room temperature. It is evident form FIG. 13 that there is substantially no change in the spectra for the treated specimen over a period of three years at room temperature.

EXAMPLE 13

Figure 14:
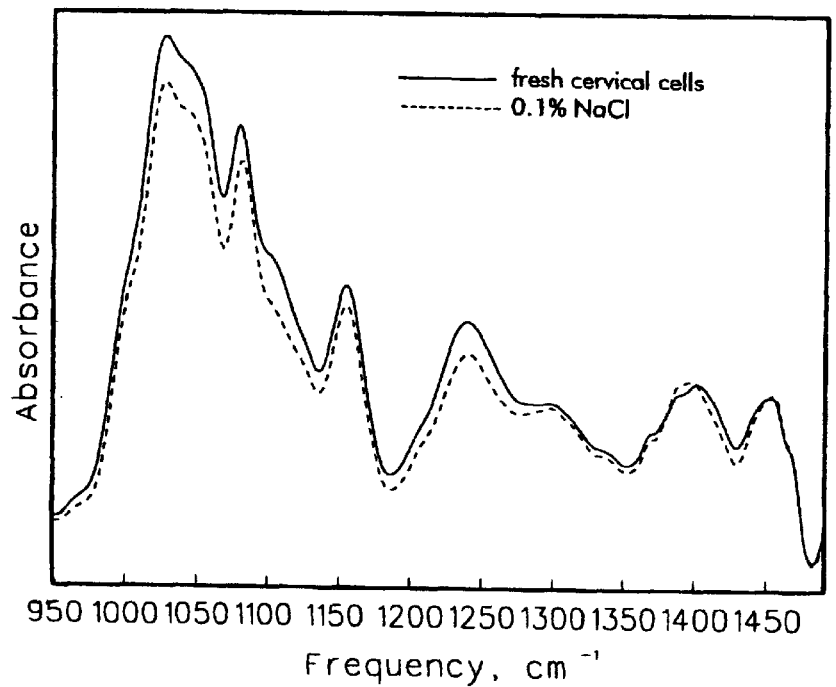
FIG. 14 shows an infrared spectra in the frequency region 950 to 1500 $cm^{-1}$ obtained from a fresh, exfoliated cervical cell specimen which has been diagnosed as moderate dysplasia and immediately after suspending the specimen in 0.1% NaCl solution.

A specimen of fresh, normal healthy, exfoliated cervical cells which had been diagnosed as moderate dysplasia was obtained. Portions were immediately suspended in normal saline solution and in 0.1% NaCl solution and then subjected to infrared spectroscopic analyses. The infrared spectra obtained are shown in FIG. 14. It is believed that the changes in the spectrum of the 0.1% NaCl solution treated specimen are the result of the osmotic lysis of the cervical cells in the hypotonic solution with the concentration of the NaCl too far below the physiological concentration of NaCl (about 0.9%) in common biological cells.

REFERENCES:

1. Rigas, B., Morgello, S., Goldman, I. S., and Wong, P. T. T. Proc. Natl. Acad. Sci. USA, 87:, 8140–8144 (1990).
2. Wong, P. T. T., Wong, R. K., Caputo, T. A., Godwin, T. A., and Rigas, R. Proc. Ntl. Acad. Sci. USA, 88: 10988–10992 (1991).
3. Rigas, B. and Wong, P. T. T. Cancer Research, 52: 84–88 (1992).
4. Wong, P. T. T., Wong, R. K., and Fung Kee Fung, M. Appli. Spectrosco., 47: 1058–1063 (1993).
5. Wong, P. T. T., Lacelle, S., and Yazdi, H. M. spectroscopy. Appli. Spectrosc., 47: 1830–1836 (1993).
6. Fung Kee Fung, M., Senterman, M. K., Mikhael, N. Z., Lacelle, S., and Wong, P. T. T. Biospectroscopy 2: 155–165 (1996).
7 Yazdi, H. M., Bertrand, M. A., Lacelle, S., and Wong, P. T. T. Acta Cytologica, 40: 664–668 (1996).
8. Wong, P. T. T., Rigas, B. U.S. Pat. No. 5,168,162, Dec. 1, (1992).
9. Morris, B. J., Lee, C., Nightingale, B. N. Molodysky, E., Morris, L. J., Appio, R., Sternhell, S., Cardona, M., Mackerras, D. and Irwig, L. M. Gynecologic Oncology, 56: 245–249 (1995).
10. Wood, B. R., Quinn, M. A., Burden, F. R., and McNaughton, D. Biospectroscopy 2: 143–153 (1996).
11. Fung Kee Fung, M., Senterman, M. K., Eid, P., Faught, W., Mikhael, N. Z., and Wong, P. T. T. Gynecologic Oncology 66: 10–15 (1997).
12. Cohenford, M. A., Godwin, T. A., Cahn F., Bhandare, P., Caputo, T. A., and Rigas, B. Gynecologic Oncology 66: 56–65 (1997).
13. Benedetti, E., Teodori, L., Trinca, M. L., Vergamini, P., Salvati, F., Mauro, F., and Spremolla, G. Appli. Spectrosc., 44: 1276–1280 (1990).
14. Gal, J., Morjani, H., Fardel, O., Guillouzo, A., and Manfait, M. Anticancer Research 14, 1541–1548 (1994).
15. Hook, G. R., Elin, R. J., Hosseini, J. M., Swyt, C. and Fiori, C. E. J. Microscopy, 141 69–78 (1985).
16. Sinor, L. T., and Fatz, R. A. U.S. Pat. No. 5,030,560, Jul. 9, (1991).

What is claimed is:

1. A method for preserving a tissue specimen to be subject to infrared spectroscopy for detecting a malignant or premalignant anomaly, comprising:

obtaining said tissue specimen including cells, said specimen being in generally wet, fresh specimen form characteristic of tissue that has been freshly removed from a living body, within about an hour of exposure to above freezing temperature applying an inorganic salt based infrared spectral preservative by soaking said specimen in an inorganic salt solution wherein the salt is selected from the group consisting of sodium halide and potassium halide, said solution having a salt concentration in the range of about 0.5 to 3.0% by weight, removing excess liquid from the specimen by centrifuging, placing the damp specimen with excess liquid removed on an infrared optical window and drying the specimen on the window by a flow of room temperature air so as to dry the specimen and form a solid film of salt crystal over the specimen within about 2 minutes, thereby obtaining a dried, spectrally-preserved specimen which substantially maintains the spectral characteristics of said fresh specimen in a spectral range of interest after exposure to above freezing temperature.

2. A method according to claim 1 wherein the salt solution has a concentration in the range of about 0.5 to 2.0% by weight.

3. A method according to claim 2 wherein the salt is sodium chloride or potassium bromide.

4. A method according to claim 1 wherein(the air drying: is conducted so as to dry the specimen and form a solid film of salt crystal over the specimen within 1 to 2 minutes.

5. A method according to claim 4 wherein the above freezing temperature is room temperature.

6. A method according to claim 5 wherein the specimen is a tissue specimen from a female reproductive tract.

7. A method according to claim 5 wherein the specimen comprises cervical cells.

8. A method according to claim 4 wherein the above freezing temperature is room temperature.

9. A method according to claim 8 wherein the specimen is a tissue specimen from a female reproductive tract.

10. A method according to claim 8 wherein the specimen comprises cervical cells.

11. A method for preserving a tissue specimen to be subject to infrared spectroscopy for detecting a malignant or premalignant anomaly, comprising: obtaining said tissue specimen including cells, said specimen being in a generally wet, fresh specimen form characteristic of tissue that has been freshly removed from a living body, within about an hour of exposure to above freezing temperature, placing said wet, fresh specimen on the surface of crystallized water-soluble inorganic salt selected from the group consisting of sodium halide and potassium halide in the form of an infrared optical window, permitting the moisture from the wet specimen to dissolve some of the salt crystal and thus cover the specimen with the dissolved salt solution, and then drying the specimen on the crystal window by a flow of room temperature air so as to dry the specimen and form a solid film within about 2 minutes, thereby obtaining a dried, spectrally preserved specimen which substantially maintains the spectral characteristics of said fresh specimen in a spectral range of interest after exposure to above freezing temperature.

12. A method according to claim 11 wherein the salt is sodium chloride or potassium bromide.

13. A method according to claim 12 wherein the air drying is conducted so as to dry the specimen and form a solid film of salt crystal over the specimen within 1 to 2 minutes.

* * * * *